United States Patent
Van Pelt et al.

[11] Patent Number: 5,750,992
[45] Date of Patent: May 12, 1998

[54] METHOD TO COMPENSATE FOR INTERFERENCES TO MERCURY MEASUREMENT IN GASES

[75] Inventors: Vince Van Pelt, Tuscumbia; Sandra J. Meischen, Florence, both of Ala.; Clifford J. Timpson, Tiverton, R.I.

[73] Assignee: Tennessee Valley Authority

[21] Appl. No.: 715,531

[22] Filed: Sep. 18, 1996

[51] Int. Cl.$^6$ .......................... G01N 21/17; G01N 21/33
[52] U.S. Cl. .................................... 250/372; 250/373
[58] Field of Search .................... 250/372, 373

[56] References Cited

U.S. PATENT DOCUMENTS

| | | | |
|---|---|---|---|
| 3,173,016 | 3/1965 | Williston et al. | 250/373 |
| 3,178,572 | 4/1965 | Williston | 250/373 |
| 3,852,604 | 12/1974 | Grengg | 250/373 |

*Primary Examiner*—Edward J. Glick
*Attorney, Agent, or Firm*—Robert A. Petrusek

[57] ABSTRACT

The present invention relates to methods and means including a process and system for producing an elemental-mercury-free reference flue gas which is used to obtain background photometric measurements thereby eliminating the photometric interferences of flue gas components to the photometric measurement of mercury. In the process, elemental mercury is selectively removed from a portion of a gaseous stream (the reference portion) and the intensity of radiation absorbed is measured by a UV spectrometer on the resulting mercury-free reference gas, and thereafter the concentration of mercury in the remainder of the gaseous stream is determined through utilization of the ratio of the transmitted radiation of the mercury-containing flue gas with respect to that of the mercury-free reference portion of the gaseous stream. The mercury concentration can then be determined without interference by other absorbing moieties at 254 nm in the flue gas. The gist underlying the inventive concept of the instant invention relates to use of a porous bed of gold-coated material to effectively remove mercury from the reference portion of the gaseous stream without altering the composition of other radiation-absorbing components therein at the wavelengths utilized for measuring mercury. An important feature of this process is that it can be used to measure elemental mercury in a flue gas upon extractive sampling from a flue stack or after the extractive sample undergoes a process to convert the mercury species in the stream to elemental mercury prior to a total mercury measurement. The ability of the instant invention to monitor mercury in the presence of interfering agents is an essential feature for mercury emission control and for compliance by fossil-fueled industries and waste combustors.

6 Claims, 1 Drawing Sheet

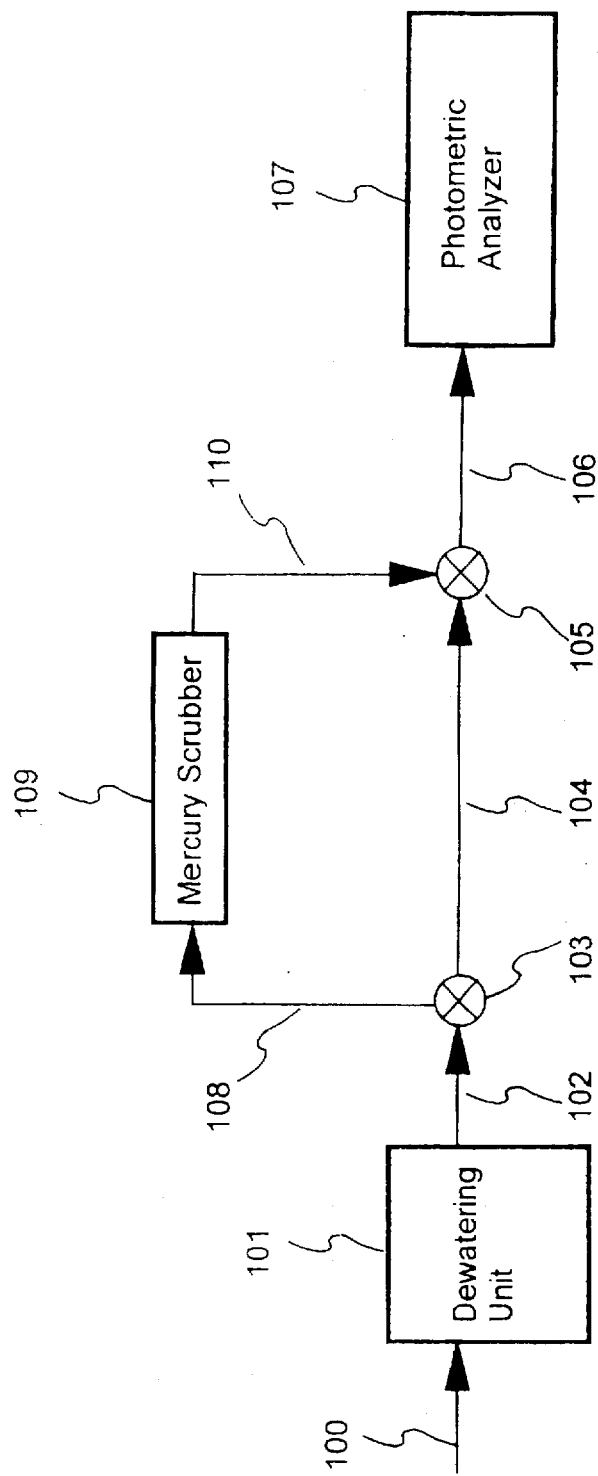

METHOD TO COMPENSATE FOR INTERFERENCES TO MERCURY MEASUREMENT IN GASES

The invention herein described may be manufactured and used by or for the government for governmental purposes without the payment to us of any royalty therefor.

INTRODUCTION

The present invention relates to the contribution of combustion sources to the mercury global cycle. Mercury from natural and anthropogenic sources recycles in the environment and collects in terrestrial and aquatic species, ultimately acting as a toxic exposure source in the food web. Numerous states have reported increases in fish advisories due to mercury. Mercury is listed as a hazardous air pollutant (HAP) in Title III of the Clean Air Act Amendments of 1990 for which EPA is mandated to evaluate emissions and health risks. Regulatory guidelines for mercury emissions from municipal waste combustors were established by EPA in 1995. Medical waste incinerators expect regulation in 1997. Another source of mercury emissions is coal-fired combustors, which face imminent regulation by federal and state agencies. EPA's mercury report is due to Congress in December 1996 and may determine whether the Clean Air Act Amendment Title III (CAAA Title III) be extended to coal-fired combustors. An increase in monitoring requirements for mercury and more restrictive controls on air toxics are anticipated which, in turn, will result in higher operational costs for these industries. Accordingly, there exists a real and eminent need for low cost, accurate technology for monitoring mercury attendant operation of such combustors and other resulting gaseous releases to the environment.

BACKGROUND OF THE INVENTION

1. Field of the Invention

This invention relates to a quick and relatively inexpensive method and means for removing the photometric contribution of radiation-absorbing interferences to the photometric measurement of mercury in gas streams, including flue gases. In particular, the mercury is removed from at least a portion, or sample of flue gas stream or the like by absorption onto a solid mass to thereby produce a resulting reference portion of flue gas on which is thereafter performed a reference measurement or zero point. Subsequent mercury measurements on at least a portion of the remaining untreated portion of raw flue gas provide a measure of mercury therein without interference from said other radiation-absorbing components.

2. Description of the Prior Art

Current methods for measuring mercury in flue gas, employ techniques which first concentrate such mercury in trapping solutions. The degree of concentration necessary in such techniques makes sampling very time-consuming, difficult and complex, and requires expert staff on site. Subsequent laboratory analysis of the resulting concentrated solutions slows data availability to days or even weeks, and measurement uncertainties plague results often due to inabilities to achieve mass balances. The determination of different mercury species (elemental and ionic) by absorption in solutions is difficult, especially in flue gas resulting from coal combustion because the mercury concentration is low and such resulting flue gas contains large amounts of $SO_2$ which can disturb analysis. A particular disadvantage of all batch methods is that the time resolution obtained is no better than 30 minute mean values.

In view of the consideration and problems, supra, it should be appreciated by those skilled in this art that there is a definite need for economical methods which accurately measure and speciate mercury in flue stack gas streams in real time at various fossil-fueled combustors, including power plants, to measure mercury emissions and identify effective control technologies.

Mercury is evolved in combustion processes of fossil-fueled and waste combustion industries thereby generating gaseous mixtures which typically contain compounds such as $NO_x$, $O_2$, $H_2O$, $CO_2$, and $CO$. Other gases such as $SO_2$, $HCl$, $Cl_2$, $H_2S$ and $NH_3$ and volatile metals and organics also may be present depending on the type of fuel combusted. Flue gases of coal combustors typically contain $O_2$, $CO_2$, $CO$, $NO$, $NO_2$, $SO_2$, $HCl$, $N_2O$, $H_2O$ and mercury species as well as many trace components.

One approach to measuring mercury in gas streams emitting from such combustion process is to detect its absorbance of light (ultraviolet) at 254 nm where elemental mercury has a narrow band of absorptivity. As those skilled in this art appreciate, the Beer-Lambert law (see equation (1) below) quantitatively expresses the dependence of the absorption of radiation with a constant wavelength on the concentration of the test substance, on the absorption coefficient which is characteristic for the test substance, the wavelength of the radiation used and the experimental conditions, and on the thickness of the absorbing layer:

$$I = I0 \; 10^{-A} = I0^{-10-abc} \tag{1}$$

where

I=intensity of the radiation transmitted through the sample layer,

I0=intensity of the incident radiation passing through analyte-free sample cell, A=absorbance of the sample, equal to the product of a, b and c defined as a=a constant for the radiation-absorbing material, the absorptivity for unit concentration at the wavelength of the incident radiation in L/mole-cm, b=the length of the sample through which the radiation passes, cm, and c=the concentration of the radiation-absorbing material, mole/L.

In determining the concentration of the analyte, only the ratio of I to I0 is important and not their absolute values. This ratio, I/I0, is called the transmittance T. Equation (1) expressed in decadic logarithms becomes:

$$-\log(I/I0) = -\log T = A = abc \tag{2}$$

Typically, the radiation intensities I and I0 are not measured simultaneously. For example, the measured intensity of a gaseous matrix is determined by referencing the intensity of the radiation of the gaseous matrix to the intensity of radiation measured when the sample cell is purged of all absorbing gases. If, however, more than one gas of the matrix absorbs at the measuring wavelength then Beer's law dictates that the absorbance of the matrix is the sum of the absorbances of all the radiation-absorbing components of the matrix.

Coal-fired utility flue gas most times contains sulfur dioxide as a congeneric impurity which absorbs ultraviolet light over a rather broad range, including, unfortunately, 254 nm. Consequently a measurement of radiation absorption at 254 nm will include contributions from mercury as well as from the sulfur dioxide component in the flue gas. Additionally, sulfur dioxide concentrations ranging from 100 to 1500 ppm can overpower typical mercury concentrations between 0 to 10 ppb.

In our early work on this project, an instrument was found which could theoretically measure mercury in the presence of sulfur dioxide by electronically subtracting the sulfur dioxide intensity measured at 313 nm from the intensity measured at 254 nm, leaving as an indicator, only the mercury absorptivity contribution at 254 nm. This is possible since the molar absorptivity of sulfur dioxide at 254 and 313 nm are approximately the same.

Specifically, in U.S. Pat. No. 3,306,156, Feb. 28, 1967, Glasser, et al., an instrument is described which can measure a radiation absorbing analyte in the presence of another radiation absorbing gas wherein the two variables characterize the sample and cause radiation absorption to a different extent at two different preselected bands of radiation of different wavelengths. For example, and again, in our early work on the instant invention it was found that elemental mercury in a gaseous mixture which mixture also contains sulfur dioxide, can be measured using the method and apparatus taught in '156, supra. It has further been found that the molar absorptivity of sulfur dioxide is approximately the same at 313 nm as it is at 254 nm. Consequently, the sulfur dioxide contribution to the elemental mercury measurement in the aggregate at 254 nm is effectively nulled by first determining the $SO_2$ radiation intensity at 313 nm and then, electronically removing this value from the aggregate measurement observed for the $SO_2$ absorbed at 254 nm. Consequently, the apparatus described in '156, supra, was modified to effect better control voltage surges and the temperature of the sampling cell and has been used in combination with our new system or means to measure elemental mercury at levels as low as 0.2 ppb in the laboratory without interference even when the $SO_2$ levels were as high as 1500 ppm, i.e., 7 logs greater.

An important complication with this measurement approach was discovered during our later work. That is, although $NO_2$, a common component of flue gas, is transparent to ultraviolet light at 254 nm it does exhibit a positive absorbance at 313 nm. Consequently, the net effect when following the techniques and procedures used in our early work of electronically subtracting the radiation absorbed at 313 nm (composed of $SO_2$ and $NO_2$ absorbances) from that at 254 nm (composed of $SO_2$ and Hg) was to effect a reduction of the apparent elemental mercury concentration compared to the actual concentration therein. Upon making this discovery, re the effect of absorbance of $NO_2$ at 313 nm, the first alternative approach which was given consideration was a method whereby an independent and simultaneous nitrogen dioxide measurement could be incorporated into the mercury determination, however, the concentration of nitrogen dioxide is not typically monitored at most combustors. Nitrogen dioxide concentrations in coal-fired combustors typically can vary anywhere from 0 to about 50 ppm. In addition, it is quite probable that other yet uncharacterized compounds in flue gas may absorb at 254 nm and/or at 313 nm which could interfere with the apparent mercury concentration. Accordingly, it was early on concluded that it would be advantageous to have or develop an uncomplicated, inexpensive, and accurate method to measure the concentration of mercury in the presence of interfering radiation-absorbing components including both $SO_2$ and $NO_2$ in flue gases and the like.

It has been known since ancient times that gold readily interacts with and retains elemental mercury at normal temperatures. The resulting accumulated mercury can be quantitatively desorbed by heating the gold to ~700° C. This property is applied in some commercially-available analytical instruments in which the mercury is concentrated by the gold, released by heating and then flushed into a mercury measuring device. For example, the Tekhran mercury analyzer 2537A concentrates mercury on a gold adsorbent. NOTE: Any references made herein to materials and/or apparatus which are identified by means of trademarks, trade names, etc., are included solely for the convenience of the reader and are not intended as, or to be construed, an endorsement of said materials and/or apparatus. The amalgamated mercury is thermally desorbed and detected using Cold Vapor Atomic Fluorescence Spectrometry.

In U.S. Pat. No. 5,026,652, June 1991, Huber, teaches the analysis of mercury by collecting mercury in fluids in a quartz tube fitted with a gold net, heating to convert the mercury to the atomic state, and thereafter cooling and preparing for analysis by Atomic Absorption Spectrometry. U.S. Pat. No. 3,714,562, Jan. 30, 1973, McNerney, teaches that mercury in air can be detected by adsorbing the mercury onto a thin layer of gold, detecting the change in resistance of the gold layer, and heating to remove the mercury from the gold layer. It should be noted that, although these methods can concentrate and/or measure mercury in ambient air, the extremely aggressive conditions found in a flue gas stream present several challenges to direct measurement using gold as a collector. These conditions include for example, temperatures ranging from 50°–135° C. at or juxtaposed the point of mercury measurement, and the varying concentrations of $SO_2$ and HCl which are dependent on combustor loading and the type or source of coal. For instance, a combination of high moisture levels, i.e. ranging from 7 to 10% and the presence of HCl make the flue gas particularly corrosive. The presence of mercuric chloride in the flue gas can further complicate the use of gold due to the uncertainty of its interaction therewith. Poor mass balance quantification of mercuric chloride suggests that it is either partially adsorbed on or desorbed from the gold collector medium.

The present invention and the practice thereof relates to a heretofore unrecognized, new, and novel approach to the use of gold for purposes of determining the levels of Hg in gas streams. Unlike the processes described above, wherein the intent is to recover mercury for measurement, the instant, new invention utilizes gold to remove elemental mercury in order to generate a mercury-free reference gas from a flue gas stream and thereafter uses the resulting reference gas to null the effects of interfering agents on photometric measurement of mercury, regardless of composition or concentration of the interfering agents. In the practice of the instant new invention, questions relating to partial adsorption or desorption of mercuric chloride with the gold are immaterial since mercuric chloride is transparent at 254 nm and its presence in the reference flue gas does not interfere with the measurement of elemental mercury. Specifically, a sample from the flue gas stream is directed through a cartridge containing a gold-coated substrate which removes substantially all the elemental mercury in the flue gas. Consequently this mercury(Hg°)-free gas is used as the reference or zeroing gas for the instrument. Functionally, the effect of any radiation-absorbing component remaining in the mercury-free flue gas at 254 nm, 313 nm, or both is nulled. Therefore, the presence of elemental mercury can be measured in the flue gas without interference from other radiation-absorbing components in the flue gas such as $SO_2$ and $NO_2$.

As noted above, in a coal-fired flue stack gas, the concentration of sulfur dioxide can range from 100–1500 ppm and can literally swamp the concentration of mercury which usually ranges up to about 4 ppb but may range in amounts up to about 10 ppb. For purposes of making the instant invention, it has been ascertained that a 10% change in sulfur dioxide in a flue gas having an initial concentration of 1500 ppm could adversely affect the resulting mercury measurement by −1.5 ppb. Therefore, it is anticipated that the best use of this invention would be the incorporation into a system of the type described in the discussion of '156, supra. The relatively high and constantly varying concentrations of $SO_2$ which oftentimes may be found in a coal-fired utility flue gas would require use of such a method which removes the radiation-absorbing $SO_2$ contribution to mercury measurement by subtracting the intensity of radiation absorbed at 313 nm from that at 254 nm.

In regards to the observation and finding that the presence of $NO_2$ interferes with the aforementioned $SO_2$ compensation mechanism, it should be further appreciated that in the practice of the instant, new, and novel invention, a first sample of the flue gas stream is directed through a cartridge containing a gold-coated substrate thereby removing substantially all the elemental mercury in the flue gas to produce a mercury-free reference gas with which to zero the instrument. Although this procedure allows for nulling of the effect of $NO_2$ on top of the effect contributed by the $SO_2$ at 313 nm, it does not have built therein, as does the $SO_2$ portion of the instant new invention, a compensating ability for variations of $NO_2$ content in the stack gas during the time comprising the sampling period, or for that matter for times therebefore or thereafter. Nonetheless, the principal concern of compensating for the value of $NO_2$ absorption substantially accomplishes the desired objectives of the instant invention since (see Examples I, III, and IV, infra) the concentration of $NO_2$ in a coal-fired utility flue stack gas typically ranges upward to 50 ppm and a 10% change in such a concentration during the zeroing of the instrument on the mercury-free flue gas will not be significant, i.e., a 10% change in a 50 ppm $NO_2$ flue gas would affect the mercury reading by no more than 0.05 ppb, a value that is within instrument error.

SUMMARY OF THE INVENTION

The present invention utilizes a previously unrecognized application of gold to remove elemental mercury from a flue gas sample and produce a reference gas for a zero point calibration for the photometric measurement of elemental mercury. In our early work, an instrument was used for the measurement of mercury of the type described in '156, supra which compensated for the radiation absorbed by $SO_2$ at the measurement wavelength of mercury, 254 nm. This was accomplished by electronically removing the $SO_2$ absorption occurring at 254 nm by subtracting the like absorption of $SO_2$ occurring at 313 nm.

However, in our later work, wherein it became clear that coal-fired utility stack gases contain $NO_2$ as well as mercury and sulfur dioxide, it was discovered that although such nitrogen dioxide does not affect the $SO_2$ absorbance at 254 nm, it does have a positive absorbance along with the $SO_2$ at 313 nm. Therefore, the first method to compensate for the interference of $SO_2$ introduces an interference from $NO_2$ and the net effect is an inaccurate measurement of elemental mercury. Thus, it was concluded that if a system such as that described in '156 supra is used, a method must be found to remove the absorbance contribution from nitrogen dioxide. The instant, new, and novel concept of using a zero calibration gas produced from the flue gas was investigated and found to be both a quick and reliable method to remove the nitrogen dioxide contribution. This resulted in an inexpensive, uncomplicated method to remove unwanted and deleterious effect(s) of radiation-absorbing components in flue gas during the measurement of elemental mercury at 254 nm, including compensation measurements at 313 nm or other wavelength(s).

OBJECTS OF THE INVENTION

It is therefore the principal object of the present invention to provide an uncomplicated, low cost, flexible methods and means which eliminate the absorbance contribution(s) of flue gas components, including $NO_2$ and $SO_2$ which components otherwise interfere with the measurement of mercury therein by converting a portion of said flue gas to a mercury-free reference gas.

Another object of the instant invention is to provide a process whereby a relatively simple, low-cost photometer can be used to accurately monitor extremely low levels of elemental mercury concentrations in gaseous matrices such as may be found in a coal-fired combustor flue stack.

Still another object of the instant invention is to provide a simple, economical method and/or means to prolong the useful life-span of the mercury scrubber used in the practice of said invention for purposes of effecting said mercury-free reference gas.

A further object of the instant invention is to provide a flexible method and means which may be incorporated into any continuous emissions monitor for mercury for the removal of measurement interferences.

A still further object of the instant invention is to provide a process which may be used to compensate for background interferences generated by the use of a converter to reduce all mercury species to the elemental form as a component of a sensor system configured to monitor total, elemental, and ionic mercury in gases emitted from combustion of natural and anthropogenic sources.

Still another object of the present invention is to provide an apparatus which may be used to compensate for background interferences generated by the use of a converter to reduce all mercury species to the elemental form as a component of a sensor system configured to monitor total, elemental, and ionic mercury in gases emitted from combustion of natural and anthropogenic sources.

Still further and more general objects and advantages of the present invention will appear from the more detailed description set forth below, it being understood, however, that this more detailed description is given by way of illustration and explanation only, and not necessarily by way of limitation since various changes therein may be made by those skilled in take art without departing from the true spirit and scope of the present invention.

DESCRIPTION OF THE DRAWING

The present invention, together with further objectives and advantages thereof, will be better understood from a consideration of the following description taken in connection with the accompanying drawing and examples in which the FIGURE is a flowsheet generally illustrating the principles of our new and novel method for removing the photometric contribution of radiation-absorbing interferences to the photometric measurement of mercury in flue gas streams.

Referring now more specifically to the FIGURE, the flue gas sample stream from a sample source (not shown) flows via line 100 to de-watering unit 101 wherein the water is removed from the sample. Line 102 feeds the resulting de-watered sample stream to first transfer valve 103 which during a measuring cycle directs the sample stream via line 104 to second transfer valve 105 which during a measuring cycle directs the sample stream from line 104 to photometric analyzer 107 via line 106 for mercury measurement. During a zero cycle first transfer valve 103 directs the sample stream to mercury scrubber 109 via line 108 wherein a noble metal-coated substrate removes the mercury from the sample stream thereby resulting in or effecting a reference stream. Line 110 feeds the resulting reference stream to second transfer valve 105 for transfer to photometric analyzer 107 via line 106 wherein a zero operation is performed. Following a zero operation the sample stream flow in line 100 is once again directed from valve 103 to line 104 through valve 105 to line 106 and thus to photometric analyzer 107 for mercury measurement. Zeroing on the mercury-free reference gas in effect nulls the interferences of radiation-absorbing components on mercury measurement in flue gas.

DESCRIPTION OF THE PREFERRED EMBODIMENTS

The instant new, novel, and unique invention, including methods, means, processes and techniques is based on the discovery that selective removal of elemental mercury from flue gas or the like can produce a reference gas for a zero point calibration at measurement wavelengths for elemental mercury. Other components in the flue gas which absorb radiation at the measurement wavelength or wavelengths for mercury are nulled when referenced to the zero point calibration. Consequently, elemental mercury in the raw flue gas can then be measured without interference from other components which absorb radiation at the same wavelength(s) used for the measurement of elemental mercury. The practice of this invention is generally carried out with a system comprising a UV photometer, a condensing unit, and preferably a gold-containing device to scrub mercury from at least a portion of the flue gas sample which later may be used for purposes of establishing the zero point calibration. The practice of this invention is not limited to a UV photometer. Also, if a condensing unit is not used to first remove water from the flue gas before it is introduced into the mercury scrubber heating of the mercury scrubber to about 70° C. to prevent water condensation therein is suggested to help prolong the useful life thereof.

In order to achieve the foregoing and other objects of the instant invention, the present invention provides a method and means for gases, including a process comprising: (a) taking a first sample, preferably in the form of a continuous stream for a predetermined period of time of the waste gas, (b) removing from the sample obtained in (a) supra, the water and water-soluble components from the stream, (c) diverting the stream through a cartridge containing therein gold-coated particulate material to effect removal of elemental mercury, (d) measuring the radiation intensity of the resultant stream of first sample as a reference gas; and (e) taking a second sample, preferably in the form of a continuous stream for a predetermined period of time of the waste gas and comparing the radiation intensity measured in said second sample of the raw flue gas to the reference gas intensity to obtain a measure of elemental mercury in the flue gas.

In order to practice the instant invention a system was devised to carry out the tests necessary therefore. Accordingly, one embodiment of such a system can comprise:

A first conduit is provided which communicates between a de-watering unit and the common input of a first transfer valve. A second conduit is provided which communicates between the normally open output of said first transfer valve and the normally open input of second transfer valve. A third conduit is provided which communicates between the common output of said second transfer valve and the input to a photometric analyzer. A fourth conduit is provided which communicates between the normally closed output of the said transfer valve and the input of a mercury scrubber. A fifth conduit is provided which communicates between the output of said mercury scrubber and the normally closed input of said second transfer valve.

During a normal measuring cycle which normally last from 20 to 30 minutes a sample stream is passed through a heated sample line to the de-watering unit which condenses and removes the water from the sample gas. This allows the mercury scrubber to be operated at ambient temperature, i.e. about 20° to 30° C. which extends its life span. A first conduit communicates between the de-watering unit and the first transfer valve which directs the sample stream to a second conduit which communicates between the first and second transfer valve. The second transfer valve directs the sample stream to a third conduit which communicates between the second transfer valve and the photometric analyzer. The sample stream is passed from the third conduit to the photometric analyzer where a photometric analysis records the amount of mercury present.

During a zero cycle which occurs every 20 to 30 minutes and lasts about 300 seconds, a first conduit which communicates between the de-watering and the first transfer valve, passes the sample stream to the first transfer valve which directs the sample stream to a fourth conduit which communicates between the first transfer valve and the mercury scrubber. The fourth conduit passes the sample stream to the mercury scrubber where a noble-metal-coated substrate absorbs the mercury but does not affect the other components of the sample stream. The mercury free sample stream now referred to as the zero reference stream passes into a fifth conduit which communicates between the mercury scrubber and the second transfer valve. The second transfer valve directs the zero reference stream to the third conduit which communicates between the second transfer valve and the photometric analyzer. At the start of the zero cycle the photometric analyzer goes into a hold mode at which time the zero reference stream passes through the analyzer for 150 seconds. At the end of the first 150 seconds the photometric analyzer zeroes itself and the transfer valves are switched back to the normal read cycle position described earlier. The photometric analyzer remains in a hold mode for another 150 seconds while the sample stream fills the analyzer. At the end of the second 150 seconds "hold," the photometric analyzer goes into a normal read mode.

EXAMPLES

In order that those skilled in the art may better understand how the present invention can be practiced, the following examples are given by way of illustration only and not necessarily by way of limitation, since numerous variations thereof will occur and will undoubtedly be made by those skilled in the art without substantially departing from the true and intended scope and spirit of the instant invention herein taught and disclosed.

The measurement instrument which was used in tests comprising the following examples was an existing UV monitoring system of the type described in '156, supra. The photometer was configured to measure mercury in the presence of sulfur dioxide. The measurement of elemental mercury at 254 nm in the presence of sulfur dioxide was accomplished by electronically nulling the sulfur dioxide contribution to the elemental mercury measurement. The sulfur dioxide absorptivity at 313 nm is comparable to that at 254 nm. Thus, by subtracting the intensity of radiation absorbed at 313 nm from that at 254 nm permitted the mercury absorbance to be measured. The instrument was calibrated for 1 ppb elemental mercury and 1500 ppm sulfur dioxide and was found to accurately measure elemental mercury at values as low as 0.2 ppb.

The measurement system also incorporated a water-condensing unit upstream of the mercury scrubber unit and the photometer. The water-condensing unit protected the mercury scrubber from water soluble components in the flue gas which could affect its mercury removal life-span and efficiency. The mercury scrubber was located upstream of the photometer and comprised a borosilicate tube of 6 mm diameter containing from 0.75 to 1 gram of gold-coated sand held in place with glass wool plugs. During operation, the flue-gas was diverted every 20 minutes through the mercury scrubber to produce a mercury-free reference gas, and the instrument response was nulled on the mercury-free flue gas during a 132 second zeroing operation. Upon completion of the zeroing cycle, measurement of the mercury in the flue gas was resumed with the resulting compensated instrument. In the examples given below the gas flow through the instrument was adjusted to 2 L/min. of dry gas matrix.

Example I

Example I illustrates the adverse influence of nitrogen dioxide on the measurement of elemental mercury [Hg°] in the presence of sulfur dioxide and the elimination of the adverse effect in the preparation and use of a mercury-free reference gas as taught by the instant invention. The gas mixture was variously composed of $NO_2$ at 46 ppm, $SO_2$ at 250 to 1000 ppm, Hg° at 1.4 ppb, and $N_2$ to make up a total flow of 2 L/min. The simulated flue gas was caused to flow either directly through the photometer for a mercury measurement or through the mercury scrubber to produce the mercury-free reference gas and subsequently through the photometer.

The nitrogen dioxide effect on the mercury reading is illustrated in tests (a)–(d) of Table 1, infra. In Table 1, "by-pass" means that the mercury scrubber was circumvented. As may be seen, fifty ppm of $NO_2$ in $N_2$ produced a mercury reading of −0.5 ppb in test (b). When elemental mercury was added at 1.4 ppb (NIST mercury permeation source) only 0.9 ppb of mercury was measured in test (c). In test (d) the gas mixture flows through the mercury scrubber but the instrument was not zeroed and the resultant reading was −0.5 ppb indicating that the mercury was removed and only nitrogen dioxide was affecting the measurement. In test (e) the gas mixture of mercury, nitrogen dioxide and nitrogen passed through the mercury scrubber and the instrument was "zeroed" on the extracted gases, nitrogen dioxide and nitrogen. Upon zeroing, the mercury measurement of the gas mix containing the mercury, nitrogen dioxide and nitrogen read correctly at 1.4 ppb. Tests (f)–(h) illustrate that as sulfur dioxide concentration was added from 250 to 500 ppm the instrument compensated for the presence of sulfur dioxide in the gaseous mixture per '156, supra. Tests (i)–(k) show that a gas mix of mercury, sulfur dioxide, nitrogen dioxide and nitrogen passed through the mercury scrubber and the instrument was "zeroed" on remaining sulfur dioxide, nitrogen dioxide and nitrogen. The sulfur dioxide concentration from 500 to 1000 ppm was effectively compensated by the instrument and correctly read the 1.4 ppb elemental mercury being generated by the NIST tube.

TABLE 1

| test | Hg° ppb | NO$_2$ ppm | SO$_2$ ppm | mercury scrubber | zero | instrument reading, ppb |
|---|---|---|---|---|---|---|
| a | — | — | — | by-pass | | 0 |
| b | — | 50 | — | by-pass | | −0.5 |
| c | 1.4 | 50 | — | by-pass | | 0.9 |
| d | 1.4 | 50 | — | in-line | | −0.5b |
| e | 1.4 | 50 | — | in-line | ✓ | 0 |
| f | 1.4 | 50 | — | by-pass | | 1.4 |
| g | 1.4 | 50 | 250 | by-pass | | 1.4 |
| h | 1.4 | 50 | 500 | by-pass | | 1.4 |
| i | 1.4 | 50 | 500 | in-line | ✓ | 0 |
| j | 1.4 | 50 | 1000 | by-pass | | 1.4 |
| k | 1.4 | 50 | 1000 | in-line | ✓ | 0 |

Example II

The measuring instrument was as described with the exception that the 313 nm measurement was disabled eliminating the compensation for the sulfur dioxide concentration as described in '156, supra. This example demonstrates that a mercury scrubber composed of gold-coated sand allows for the measurement of elemental mercury at 254 nm wavelength in presence of sulfur dioxide. It should, however, be noted that the procedure in this example is based on the premise of combustor operation parameters wherein $SO_2$ in the gas is relatively constant throughout the burn. Accordingly, the use of this method in practice assumes that fluctuations in the concentration of sulfur dioxide are substantially minimal.

The sulfur dioxide effect on the elemental mercury reading is demonstrated in tests (a)–(b) of Table 2, infra. One hundred ppm of $SO_2$ in $N_2$ produced a mercury reading of 1.9, an increase of 1 ppb over the actual concentration. In test (c) the instrument was zeroed on the reference gas produced after diverting the gas flow through the mercury scrubber, and the mercury measurement corresponds to the concentration generated by the NIST tube. The concentration of $SO_2$ was then raised to 800 ppm which produced an 8.3 ppb reading for mercury. Again, the instrument was zeroed on the reference gas produced by diverting this gas flow through the mercury scrubber and the elemental mercury concentration measurement again corresponded to that generated by the NIST tube. The process was repeated with a concentration of 1500 ppm $SO_2$ with the same result. In the final test (h), 50 ppm $NO_2$ was added to the gas matrix and in accordance with the predictions, supra, no change in elemental mercury measurement was observed.

TABLE 2

| test | Hg° ppb | SO$_2$ ppm | NO$_2$ ppm | mercury scrubber | zero | instrument reading, ppb |
|---|---|---|---|---|---|---|
| a | 0.9 | — | — | — | | 0.9 |
| b | 0.9 | 100 | — | by-pass | | 1.9 |
| c | 0.9 | 100 | — | in-line | ✓ | 0.9 |
| d | 0.9 | 800 | — | by-pass | | 8.3 |
| e | 0.9 | 800 | — | in-line | ✓ | 0.9 |
| f | 0.9 | 1500 | — | by-pass | | 8.3 |
| g | 0.9 | 1500 | — | in-line | ✓ | 0.9 |
| h | 0.9 | 1500 | 50 | by-pass | | 0.9 |

Example III

The measuring instrument was as described in the lead-in to these examples with the exception that the mercury scrubber was positioned upstream of the water-condensing unit. The mercury scrubber was heated to 70° C. to prevent water condensation within the scrubber. With this arrangement, the effects of hydrochloride gas in the presence of 10% water, and of temperature changes on the mercury scrubber containing the gold-coated sand were evaluated. As data in Table 3 infra suggests, a dry gas matrix, a lower scrubber temperature, and a reduced HCl concentration increase the lifetime of the scrubber. Test (1) shows that a lower temperature extends the breakthrough time for the mercury scrubber.

The term "breakthrough time," as used herein means and is intended to mean the time it takes the mercury scrubber to become saturated and the mercury to begin passing through it, rather than being trapped therein. The saturation, although substantially contributed by mercury may also be attributed to poisoning of the noble-metal surface by other materials such as HCl and $SO_2$.

The effect of hydrochloride gas in the presence of 10% water vapor is shown in tests (3) to (5) to reduce the breakthrough time of the mercury scrubber. In test (5), 140 ppm HCl in 10% water vapor saturated the mercury scrubber prior to introduction of the gaseous matrix containing elemental mercury, and accordingly, mercury breakthrough occurred within only 10 minutes. Based on the data in the Table 3, infra, the prediction of the useful life-span of the particular gold or sand mercury scrubber without regeneration ranges from about 40 to about 95 days, however, a regular heating interval to rejuvenate the gold affinity for mercury can be easily incorporated into the design to increase life-span of the referencing process.

Invention Parameters

After sifting and winnowing through the data herein presented, as well as other results and operations of the instant new, novel, and improved technique, including methods and means for the effecting thereof, the operating variables, including the acceptable and preferred conditions for carrying out the instant, new, and novel invention are summarized below:

| VARIABLES | OPERATING LIMITS | PREFERRED LIMITS | MOST PREFERRED LIMITS |
|---|---|---|---|
| Temp Hg° Scrubber* | 0–100° C.*** | 4–7° C. | 25–30° C. |
| Water Vapor Conc. | 0–15% | 5–10% | 7–8% |
| $SO_2$ Conc.** | 0–2500 ppm | 500–1500 ppm | 500–1000 ppm |
| $NO_2$ Conc. | 0–500 ppm | 1–100 ppm | 0–50 ppm |
| HCl Conc. | 0–200 ppm | 0–50 ppm | 0–25 ppm |

*The Hg° scrubber must be operated above the dew point temperature of the flue gas to prevent water condensation. The higher the temperature of the Hg° scrubber the less Hg° it will hold, so the shorter its operational life will be.
**Above 2500 ppm $SO_2$ the instrument compensation for $SO_2$ does not work well.
***The Hg° scrubber may be operated above 100° C., but its breakthrough time will be reduced.

While we have shown and described particular embodiments of this invention, modifications and variations thereof will occur to those skilled in the art. It is to be understood therefore that the appended claims are intended to cover such modifications and variations which are within the true scope and spirit of this invention.

TABLE 3

| Test | Wt. Au-coated sand, gms | Prior to test, saturate Au with: | Hg° conc., ppb | $H_2O$ conc., % | HCl conc., ppm | CO conc., ppm | Temp °C. | Hg° breakthrough time, hrs |
|---|---|---|---|---|---|---|---|---|
| 1 | 0.740 | — | 1.6 | — | — | — | 40 | 2.8 |
| 2 | 0.759 | — | 1.6 | — | — | — | 70 | 1.8 |
| 3 | 0.756 | — | 1.6 | 10 | 140 | — | 70 | 1.6 |
| 4 | 0.756 | — | 1.6 | 10 | 140 | 100 | 70 | 1.5 |
| 5 | 0.728 | HCl | 1.6 | 10 | 140 | — | 70 | 0.1 |

Example IV

Again, the measuring instrument is as described in the lead-in to these examples. The mercury concentration of a simulated flue gas containing 1.6 ppb (v/v) of elemental mercury, 1500 ppm $SO_2$, 50 ppm $NO_2$, 550 ppm NO, 140 ppm HCl, 14% $CO_2$, 10% $H_2O$, 7% $O_2$ was monitored continuously for 84 hours. The instrument was automatically zeroed on the elemental mercury-free reference gas obtained after flowing the simulated gas through a 6 mm ID tube containing 1.01 grams of gold-coated sand to remove elemental mercury from the gas matrix. The instrument was zeroed every 30 minutes, for a period of 132 seconds, albeit this time can be varied as long as sufficient time is allowed for the cell to be purged with reference gas prior to zeroing and is also allowed sufficient time to refill with sample gas before the resumption of measuring. The mercury generated by a NIST calibrated mercury diffusion tube was monitored at 1.6 ppb ±0.1 ppb elemental mercury for the 84 hours of the test. This example illustrates that a gold sorbent can selectively remove elemental mercury from a simulated flue gas matrix and can produce a reference gas free of elemental mercury which can be used for zero point calibration of a mercury measurement photometer.

What we claim as new and desire to secure by Letters Patent of the United States is:

1. An improved photometric measurement system for accurately determining levels of elemental mercury in sampled gases, said sampled gases comprising, in addition to said mercury, other impurities effected through the oxidation of carbonaceous materials, wherein at least one of said other impurities absorbs ultraviolet radiation at radiation wavelengths selected from the group consisting of about 254 nm, 313 nm, and mixtures thereof, said improved system comprising:

means for obtaining a first gas sample to be analyzed;

means for removing substantially all water vapor from said first gas sample;

means comprising gold coated substrate material for removing substantially all elemental mercury from said first gas sample;

means for obtaining a second gas sample to be analyzed;

photometric measurement means comprising an ultraviolet spectrophotometer for determining intensities of radiation absorbed at about 254 nm or 313 nm or both by components in said first gas sample and for determining intensities of radiation absorbed at about 254 nm or 313 min or both in said second gas sample, said second gas sample containing elemental mercury; and means for determining the concentration of mercury in said second gas sample through utilization of the ratio of the transmitted radiation at wavelengths selected from the group consisting of about 254 nm, 313 nm, and mixtures thereof of said second gas sample with respect to the transmitted radiation, at said selected wavelengths, of said first gas sample.

2. The improved photometric measurement system of claim 1, wherein said substrate material comprises sand.

3. The improved photometric measurement system of claim 2, wherein said at least one of said other impurities in said first gas sample is selected from the group consisting of $NO_2$, $SO_2$, and mixtures thereof.

4. The improved photometric measurement system of claim 3, wherein said at least one of said other impurities in said first gas sample comprises $SO_2$ and $NO_2$.

5. The improved photometric measurement system of claim 3, wherein said at least one of said other impurities comprise both $SO_2$ and at least one other component which absorbs ultraviolet radiation at 254 nm.

6. The improved photometric measurement system of claim 3, wherein said at least one of said other impurities comprise both $NO_2$ and at least one other component which absorbs ultraviolet radiation at 313 nm.

* * * * *